(12) United States Patent
Guardiani

(10) Patent No.: US 11,536,720 B2
(45) Date of Patent: Dec. 27, 2022

(54) OPTOELECTRONIC DEVICE FOR DETECTION OF A SUBSTANCE DISPERSED IN A FLUID

(71) Applicant: FTH S.R.L., Rovereto (IT)

(72) Inventor: Carlo Guardiani, Verona (IT)

(73) Assignee: FTH S.r.L., Rovoreto (IT)

( * ) Notice: Subject to any disclaimer, the term of this patent is extended or adjusted under 35 U.S.C. 154(b) by 682 days.

(21) Appl. No.: 16/479,622

(22) PCT Filed: Jan. 19, 2018

(86) PCT No.: PCT/EP2018/051296
§ 371 (c)(1),
(2) Date: Jul. 22, 2019

(87) PCT Pub. No.: WO2018/134348
PCT Pub. Date: Jul. 26, 2018

(65) Prior Publication Data
US 2021/0055293 A1    Feb. 25, 2021

(30) Foreign Application Priority Data

Jan. 23, 2017 (IT) .......................... 102017000006640

(51) Int. Cl.
*G01N 33/543* (2006.01)
*G01N 21/75* (2006.01)
*G01N 21/77* (2006.01)

(52) U.S. Cl.
CPC ....... *G01N 33/54373* (2013.01); *G01N 21/75* (2013.01); *G01N 21/7746* (2013.01); *G01N 2021/7789* (2013.01)

(58) Field of Classification Search
None
See application file for complete search history.

(56) References Cited

U.S. PATENT DOCUMENTS 6,603,560 B1 * 8/2003 Islam ................. G01N 21/7746
356/480
9,080,953 B2   7/2015 Heidrich et al.
(Continued)

OTHER PUBLICATIONS

Hedieman R et al.: "TriPleX-Based Integrated Optical Ring Resonators for Lab-on-a-Chip and Environmental Detection", IEEE Journal of Selected Topics in Quantum Electronics, IEEE Service Center, Piscataway, NJ, US, vol. 18, No. 5, Aug. 24, 2012 (Aug. 24, 2012), pp. 1583-1596, XP011466307.

(Continued)

*Primary Examiner* — Elizabeth A Robinson
*Assistant Examiner* — Ryan J Dowty
(74) *Attorney, Agent, or Firm* — Patterson Intellectual Property Law, P.C.

(57) ABSTRACT

The present invention relates to an optoelectronic device (1) for detection of a target substance dispersed in a fluid (50). The optoelectronic device comprises:—a light source (2) adapted to emit a light radiation ($L_E$) having an adjustable wavelength $\lambda_S$;—an integrated electronic circuit (100) comprising a photonic circuit (10) operatively coupled to said light source;—a control unit (9) operatively coupled to said light source and to said photonic circuit.

19 Claims, 5 Drawing Sheets

(56) References Cited

U.S. PATENT DOCUMENTS

| | | | |
|---|---|---|---|
| 9,448,181 B2 | 9/2016 | Lee et al. | |
| 2005/0110992 A1* | 5/2005 | Scherer | B82Y 20/00 |
| | | | 356/318 |
| 2007/0211985 A1* | 9/2007 | Duer | G01N 21/253 |
| | | | 422/82.11 |
| 2009/0251705 A1* | 10/2009 | Le | G01N 21/7703 |
| | | | 356/491 |
| 2016/0033412 A1* | 2/2016 | Tan | G01N 33/54373 |
| | | | 422/69 |

OTHER PUBLICATIONS

Chung-Yen Chao et al.: "Design and optimization of microring resonators in biochemical sensing applications", Journal of Lightwave Technology, vol. 24, No. 3, Mar. 1, 2006 (Mar. 1, 2006), pp. 1395-1402, XP055412235.

International Searching Authority: "PCT Notification of Transmittal of the International Search Report and the Written Opinion of the International Searching Authority, or the Declaration," PCT/EP2018/051296, dated Mar. 6, 2018 (Mar. 13, 2018) pp. 1-6.

* cited by examiner

OPTOELECTRONIC DEVICE FOR DETECTION OF A SUBSTANCE DISPERSED IN A FLUID

The present invention relates to an optoelectronic device for detection of a substance dispersed in a fluid.

In the state of the art, numerous examples of optoelectronic devices for detection of a target substance dispersed in a fluid are known.

Some optoelectronic devices of known type use an open loop detection system to detect the target substance.

An optoelectronic device of this type is described in the patent application US2012/0092650. The device described therein is provided with an optical circuit comprising one or more optical resonators, each of which comprises a ring optical path having an active surface capable of selectively absorbing the target substance.

The light emitted by a light source laser is transmitted, through the free space, to the optical circuit, conveyed through the optical resonators and transmitted, again through the free space, to a spectrum analyser.

Given that the optical path of the light in optical resonators varies as a function of the quantity of target substance absorbed selectively by the active surface of these latter, the presence or concentration of the target substance can be detected by analysing the spectrum of the light transmitted by the optical circuit.

Experience has shown how optoelectronic devices of the type indicated have numerous limitations in terms of accuracy and measurement resolution.

In fact, in these devices the measurement signal indicative of the presence or concentration of the target substance is typically characterized by a relatively high signal-to-noise ratio. Therefore, to obtain acceptable performance, very accurate control of the physical and optical characteristics of the components and of the environmental operating conditions (temperature, humidity and the like) is necessary. Consequently, practical use of these devices is often difficult and laborious.

Finally, the aforesaid currently available optoelectronic devices have numerous disadvantages in terms of structural complexity and overall dimensions and are relatively costly to achieve industrially, as they are somewhat unsuitable for production on an industrial scale in miniaturized format.

Other optoelectronic devices of known type use a closed loop detection system to detect the target substance.

An optoelectronic device of this type is described in the patent U.S. Pat. No. 9,080,953.

This device is provided with an integrated photonic circuit comprising a pair of optical resonators arranged in series along an optical path.

The light emitted by a broad spectrum laser light source (for example of Fabry-Perot type) is transmitted, through the free space, to the integrated photonic circuit and conveyed to a first optical resonator arranged to operate as an optical filter (optionally with adjustable bandpass) having a transmittance peak at a specific wavelength.

The light exiting from the first optical resonator is in part conveyed to a first photo-diode operatively connected to a control unit and in part transmitted to the second optical resonator. This latter is provided with an optical path having an active surface capable of selectively absorbing the substance to be detected.

The light radiation traveling through the second resonator is subjected to a variation (shift) of the resonance wavelength, which is a function of the quantity of substance to be detected absorbed by the active surface of the resonator.

The light exiting from the second resonator is transmitted to a further photo-diode operatively connected to a control unit.

The control unit generates control signals (for example an electric current or voltage applied to the integrated photonic circuit) to align the wavelength of the transmittance peak of the first optical resonator with the resonance wavelength of the second optical resonator. These control signals are indicative of the presence or concentration of the substance to detect.

Optoelectronic devices of the type described above without doubt offer improved performance in terms of accuracy and measurement resolution, with respect to more conventional devices.

However, currently available devices of this type are typically difficult to use practically and complex to produce industrially.

For example, the device described in the patent U.S. Pat. No. 9,080,953 requires the aforesaid resonators to have almost identical physical and optical characteristics to obtain satisfactory immunity from common mode noise. Moreover, it is necessary to provide a regulator to vary, in a controlled way, the resonance wavelength of at least one resonator by means of suitable current or voltage control signals. Therefore, it is difficult and costly to produce industrially.

The scientific papers "TriPleX-Based integrated Optical ring resonators for Lab-on-Chip and Environmental Detection", IEEE Journal of Selected Topics in Quantum Electronics, Vol. 18, no 5, September 2012, pages 1583-1596 (XP011466307) by Heideman R. et al. and "Design and optimization of micro-ring resonators in biochemical sensing applications", Journal of Lightwave Technology, Vol. 24, n° 3, March 2006, pages 1395-1402 (XP055412235) by Chung-Yen Chao et al. and the patent document U.S. Pat. No. 9,448,181B2 disclose further known examples of optoelectronic devices including ring resonating sensors.

Unfortunately, also these devices do not allow to completely overcome the above-mentioned technical issues of the state of the art.

Nowadays, there is still great need to provide optoelectronic devices for detection of a target substance dispersed in a fluid capable of offering high performance in terms of accuracy, measurement resolution, response times and, at the same time, which are relatively simple to use practically and easy to produce industrially, in miniaturized format.

Further characteristics and advantages of the present invention will become more apparent with reference to the description given below and to the accompanying figures, provided purely for explanatory and non-limiting purposes, wherein FIGS. 1-5 illustrate, by way of example, the structure and the operation of the optoelectronic device according to the invention.

FIG. 1 schematically illustrates an optoelectronic device according to the invention.

Figure 1:
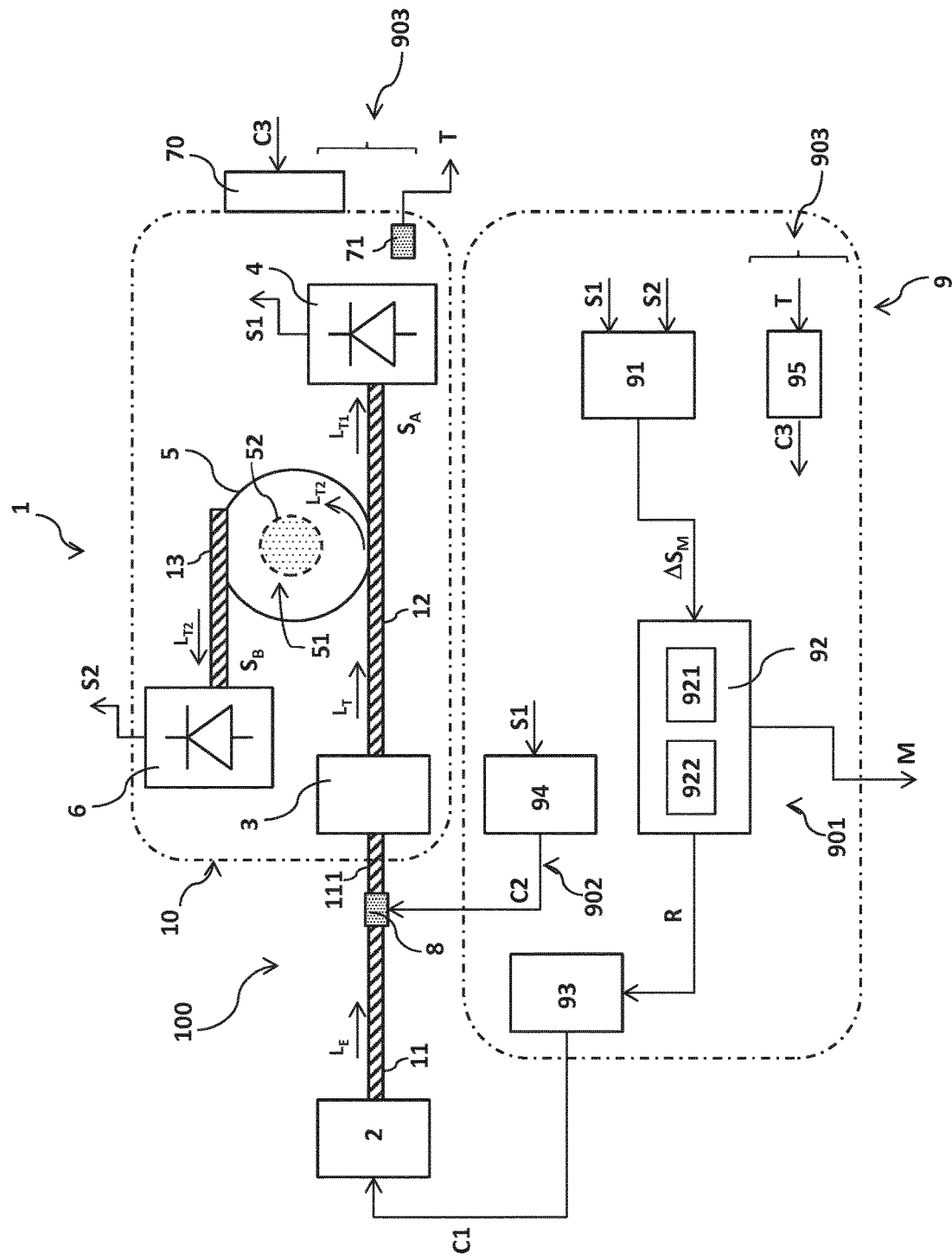
Figure 5:
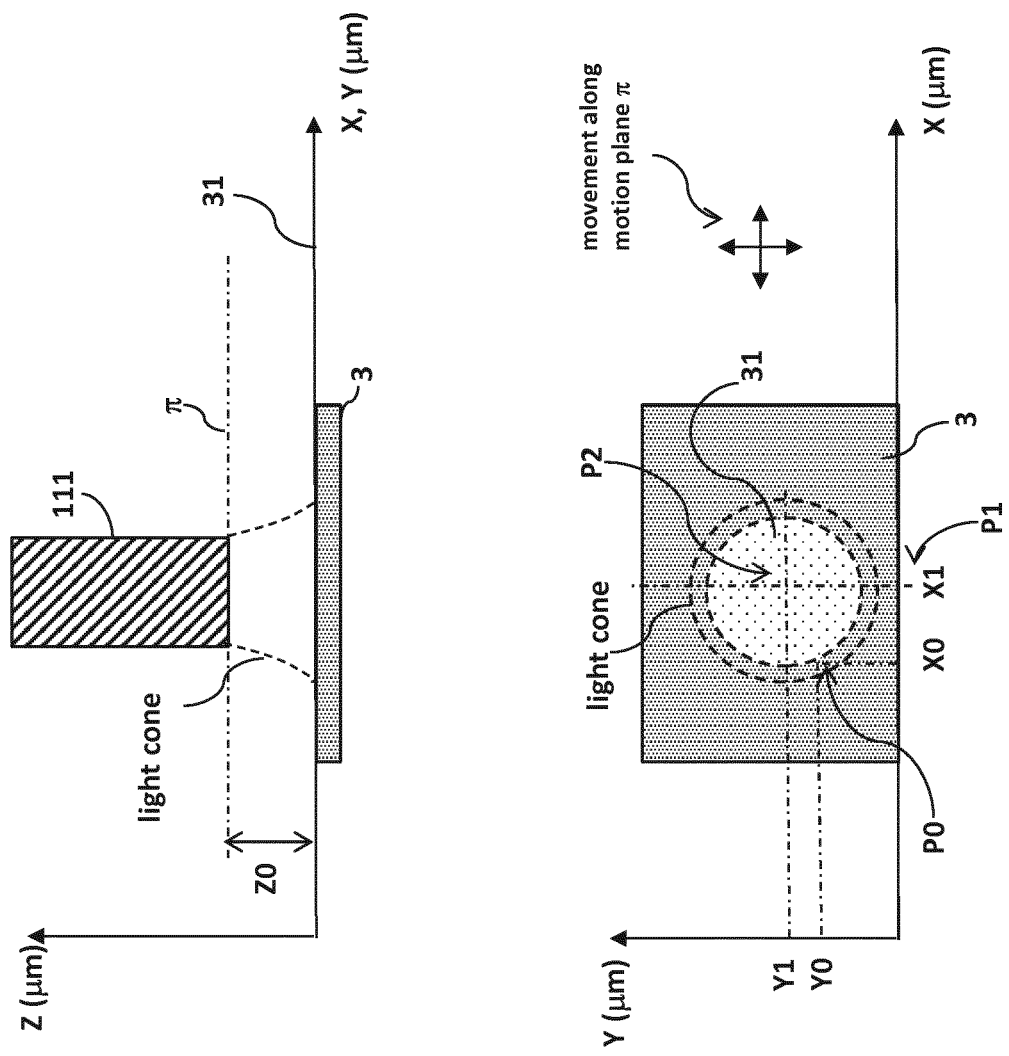

FIG. 5 includes graphical diagrams representing a calibration procedure executable by the control unit according to FIG. 1.

With reference to the aforesaid figures, the present invention relates to an optoelectronic device 1 for detection of the presence or concentration of a target substance dispersed in a fluid 50.

In principle, the target substance to be detected, by means of the electronic device 1, can be of any type, for example a material, a compound, a chemical or biological substance.

The fluid 50 can also be of any type: a liquid (for example of biological origin, a process liquid or a chemical solution) or a gas (for example a process gas).

The optoelectronic device 1 comprises a light source 2 adapted to emit a light radiation $L_E$ having an adjustable wavelength $\lambda_S$, for example with values in the order of nanometers. Preferably, the light source 2 is a laser light source, more particularly a laser source with very narrow spectrum (a few nm), for example a DFB laser.

The optoelectronic device 1 comprises an integrated electronic circuit 100 operatively coupled to the light source 2.

The integrated electronic circuit 100 can advantageously be produced industrially with known techniques for processing semiconductor materials. For example, techniques for planar processing of integrated circuits, techniques for micro-machining silicon (bulk micro-machining or surface micro-machining), or the like can be used.

The integrated electronic circuit 100 can have dimensions in the order of tens or hundreds of μm.

In the embodiments described below, the integrated circuit 100 is structurally separate from the light source 2 and coupled operatively to this latter.

However, in some embodiments of the optoelectronic device 1, the light source 2 and the integrated circuit 100 could be structurally integrated with each other, optionally also in a single integrated circuit.

The optoelectronic device 1 comprises a control unit 9 operatively coupled to the light source 2 and to the integrated circuit 100.

The control unit 9 is an electronic device that comprises a plurality of functional modules 91, 92, 93, 94, 95 that can be produced industrially in analog and/or digital mode.

If produced in analog mode, these functional modules can comprise electronic circuits (separated into distinct units or integrated with one another) arranged to perform the desired functions.

If produced digitally, these functional modules can comprise sets of software instructions, stored or storable on a data storage medium, and executable by one or more digital signal processing units (for example microprocessors) to perform the desired functions.

The control unit 9 is easy to produce industrially with known electronic circuit assembly techniques (for example assembly on PCB).

In some embodiments of the optoelectronic device 1, the control unit 9 and the integrated circuit 100 could be structurally integrated with each other, optionally also in a single integrated circuit.

The control unit 9 is adapted to provide control signals (of electric type) to the light source 2 to adjust the wavelength $\lambda_S$ of the light radiation $L_E$ emitted by this latter.

Preferably, as will be more apparent below, the control unit 9 is also adapted to carry out signal processing functions and to provide first measurement signals M indicative of a presence or concentration of the target substance dispersed in the fluid 50.

According to the invention, the integrated electronic circuit 100 comprises an integrated photonic circuit 10 operatively coupled to the light source 2.

The photonic circuit 10 comprises an optical coupler 3, preferably of the grating type (optical grating coupler).

The optical coupler 3 is operatively coupled to the light source 2 and is adapted to receive a light radiation $L_E$ emitted by the light source 2 and transmit a light radiation $L_T$.

To this end, the optical coupler 3 is provided with a first active surface 31 optically coupled with the light source 2.

Preferably, the optoelectronic device 1 comprises a first wave-guide 11 to optically couple the optical coupler 3 with the light source 2.

The optical coupler 3 is advantageously formed by a corresponding portion of the photonic circuit 10 suitably processed, for example by means of know techniques for processing semiconductor materials.

For example, the active surface 31 can have an extension about 10 μm².

Preferably, the wave-guide 11 comprises an optical fiber, for example of single mode type (SMF—Single Mode Fibers), having a core diameter of around 10 μm.

The photonic circuit 10 comprises a first detector 4 and an optical resonator 5 optically coupled with the optical coupler 3 and a second detector 6 optically coupled with the optical resonator 5.

The first detector 4 is adapted to receive a first light radiation $L_{T1}$ transmitted by the optical coupler 3, which, in general, corresponds to a first portion of the light radiation $L_T$ transmitted by said optical coupler.

The optical resonator 5 is adapted to convey and transmit a second light radiation $L_{T2}$, which, in general, corresponds to a second portion of the light radiation $L_T$ transmitted by the optical coupler 3. The second detector 6 is adapted to receive the second light radiation $L_{T2}$ transmitted by the optical resonator 5.

In general, the above-mentioned first and second portions $L_{T1}$, $L_{T2}$ of the light radiation $L_T$ transmitted by the optical coupler 3 are complementary one to another (in quantitative terms). As it will better emerge from the following, the quantitative value of said first and second portions of light radiation $L_{T1}$, $L_{T2}$ basically depends on the wavelength of the light radiation $L_T$ transmitted by the optical coupler 3.

When the wavelength of the light radiation $L_T$ is far from the resonance wavelength $\lambda r$ of the optical resonator, the first portion of light radiation $L_{T1}$ received by the detector 4 has a maximum value whereas the second portion of light radiation $L_{T2}$ conveyed by the optical resonator 5 and transmitted to the second detector 6 has a minimum value. In this case, the first portion of light radiation $L_{T1}$ may substantially correspond to the full amount light radiation $L_T$ transmitted by the optical coupler 3 whereas the second portion of light radiation $L_{T2}$ may be substantially null.

When the wavelength of the light radiation $L_T$ is at the resonance wavelength $\lambda r$ of the optical resonator, the first portion of light radiation $L_{T1}$ received by the detector 4 has a minimum value (which may be substantially null) whereas the second portion of light radiation $L_{T2}$ conveyed by the optical resonator 5 and transmitted to the second detector 6 has a maximum value (which may substantially correspond to the full amount of light radiation $L_T$ transmitted by the optical coupler 3). In this case, the second portion of light radiation $L_{T2}$ may substantially correspond to the full amount light radiation $L_T$ transmitted by the optical coupler 3 whereas the first portion of light radiation $L_{T1}$ may be substantially null.

Preferably, the optoelectronic device 1 comprises a second wave-guide 12 to optically couple the optical coupler 3 with the detector 4 and the optical resonator 5.

Preferably, the wave-guide 12 is formed by a corresponding portion of the photonic circuit 10 suitably processed, for example by means of known techniques for processing semiconductor materials. For example, the wave-guide 12 can have a width of around 0.5 µm and a length of a few tens of µm.

The detector 4 is adapted to receive the first light radiation $L_{T1}$ and provide first detection signals S1 (of electric type) indicative of the optical power $S_A$ of the said light radiation.

The detector 4 is operatively coupled with the control unit 9 to transmit the aforesaid detection signals S1 to this latter.

Preferably, the detector 4 comprises a photo-diode, advantageously formed by a corresponding portion of the photonic circuit 10 suitably processed, for example by means of known techniques for processing semiconductor materials.

The operative coupling between the detector 4 and the control unit 9 can also be produced using known techniques for electrically coupling integrated circuits and electronic devices.

The optical resonator 5 comprises a ring optical path 51 (ring optical resonator).

The optical resonator 5 is adapted to convey the light radiation $L_{T2}$ along the ring optical path 51 and transmit said light radiation to the detector 6.

At least at one portion of the ring optical path 51, the optical resonator 5 is provided with a second active surface 52 destined to come into contact with the fluid 50.

The active surface 52 of the optical resonator 5 comprises a material capable of selectively absorbing the target substance to be detected. This material can be of known type.

Given that the refraction index of the material at the optical path 51 varies when the active surface 52 absorbs a quantity of the target substance, the resonance wavelength $\lambda r$ of the optical resonator 5 varies as a function of the quantity of target substance absorbed by the active surface 52.

In fact, as is known, based on the known properties of ring optical resonators, the resonance wavelength $\lambda r$ of the optical resonator 5 can be expressed by the relation:

$$\lambda r = 2\pi r^* \text{neff}/m$$

where r is the radius of the ring optical path 51, neff is the refraction index of the material at the active surface 52 and m is an integer (1, 2, 3, 4 . . . )

Absorption of the target substance by the active surface 52 of the optical resonator 5 thus determines a variation (shift) $\Delta\lambda_{SHIFT}$ of the resonance wavelength $\lambda r$ of the light radiation $L_{T2}$ that travels along the optical path 51.

As is known, this variation $\Delta\lambda_{SHIFT}$ can be expressed by the relation:

$$\Delta\lambda_{SHIFT} = \lambda r^* (\Delta\text{neff}/\text{neff})$$

where $\Delta$neff is the variation of the refraction index due to the material absorbed at the active surface 52.

Preferably, the optical resonator 5 is formed by a corresponding portion of the photonic circuit 10 suitable processed, for example by means of known techniques for processing semiconductor materials. For example, the optical resonator 5 can have a ring optical path 51 with radius r around 50 µm.

The second detector 6 is adapted to receive the second light radiation $L_{T2}$ and provide second detection signals S2 (of electrical type) indicative of the optical power $S_B$ of said light radiation $L_{T2}$.

Preferably, the optoelectronic device 1 comprises a third wave-guide 13 to optically couple the optical resonator 5 with the second detector 6.

Preferably, the wave-guide 13 is formed by a corresponding portion of the photonic circuit 10 suitably processed, for example by means of known techniques for processing semiconductor materials. For example, the wave-guide 13 can have a width of around 0.5 µm and a length of a few tens of µm.

The second detector 6 is operatively coupled with the control unit 9 to transmit the aforesaid detection signals S2 to this latter.

Preferably, the second detector 6 comprises a photo-diode, advantageously formed by a corresponding portion of the photonic circuit 10 suitably processed, for example by means of known techniques for processing semiconductor materials. The operative coupling between the second detector 6 and the control unit 9 can also be produced using known techniques for electrically coupling integrated circuits and electronic devices.

According to the invention, the control unit 9 is adapted to receive and process the first and second detection signals S1, S2 and to provide, in response to the aforesaid detection signals S1, S2, first control signals C1 to adjust the wavelength $\lambda s$ of the light radiation $L_E$ emitted by the light source 2 so that the difference of optical power $\Delta S = S_A - S_B$ between the light radiations $L_{T1}$, $L_{T2}$ takes a minimum value (for example $\Delta S = 0$).

Preferably, the optoelectronic device 1 comprises a first control loop 901 to adjust the wavelength $\lambda s$ of the light radiation $L_E$ emitted by the light source 2.

Preferably, the control loop 901 comprises the photonic circuit 10 and a measurement module 91, a signal processing module 92 and a first control module 93 of the control unit 9.

The measurement module 91 is operatively associated with the detectors 4, 6.

The measurement module 91 is adapted to receive the first and second detection signals S1, S2 and to provide, in response to said first and second detection signals, second measurement signals $\Delta S_M$ indicative of a difference of optical power $\Delta S$ between the light radiations $L_{T1}$, $L_{T2}$ received respectively by the detectors 4, 6. For example, the measurement module 91 can S2 (for example the signal S2).

The signal processing module 92 is operatively associated with the measurement module 91. The signal processing module 92 is adapted to receive the measurement signals $\Delta S_M$ and to provide, in response to said measurement signals, regulation signals R indicative of a reference wavelength for the light source 2.

Advantageously, the reference wavelength, calculated by the signal processing module 92, is a wavelength in the vicinity of a resonance wavelength $\lambda r$ of the optical resonator 5 at which the difference of optical power $\Delta S$ between the light radiations $L_{T1}$, $L_{T2}$ takes a minimum value ($\Delta S = 0$).

Preferably, the signal processing module 92 advantageously comprises a trans-impedance amplifier module 921 and an integrator module 922 arranged in cascade, as illustrated in FIG. 1.

The first control module 93 is operatively associated with the signal processing module 92. The first control module 93 is adapted to receive the regulation signals R and to provide, in response to said regulation signals, the first control signals C1 to adjust the wavelength $\lambda s$ of the light radiation $L_E$ emitted by the light source 2 so that the difference of optical power $\Delta S$ between the light radiations $L_{T1}$, $L_{T2}$ takes a minimum value ($\Delta S = 0$). For example, the control module 93 can comprise a controller for a light source laser.

Preferably, the control unit 9 is adapted to provide, in response to the aforesaid detection signals S1, S2, also first measurement signals M indicative of a presence or concentration of the target substance.

According to some embodiments of the invention, the first measurement signals M can be provided directly by the signal processing module 92, as illustrated in FIG. 1.

According to some embodiments of the invention, the first measurement signals M can be provided by a further signal processing module (not illustrated) of the control unit 9, which can advantageously be arranged to receive the detection signals S1, S2 and to provide, in response to said detection signals, the first measurement signals M.

Figure 2:
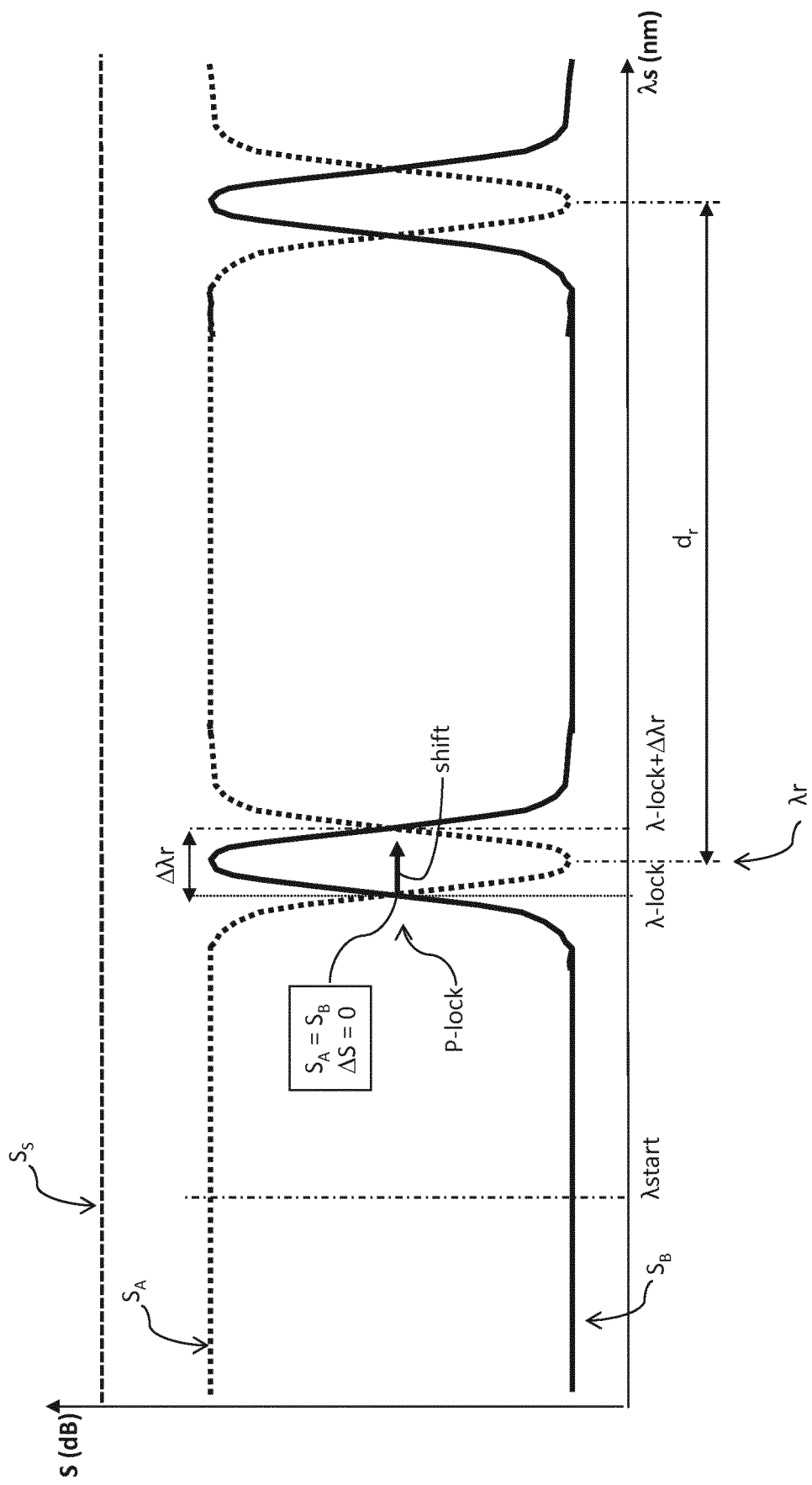
FIG. 2 is a graphical diagram schematically illustrating a control operation of the optoelectronic device according to FIG. 1.
Figure 3:
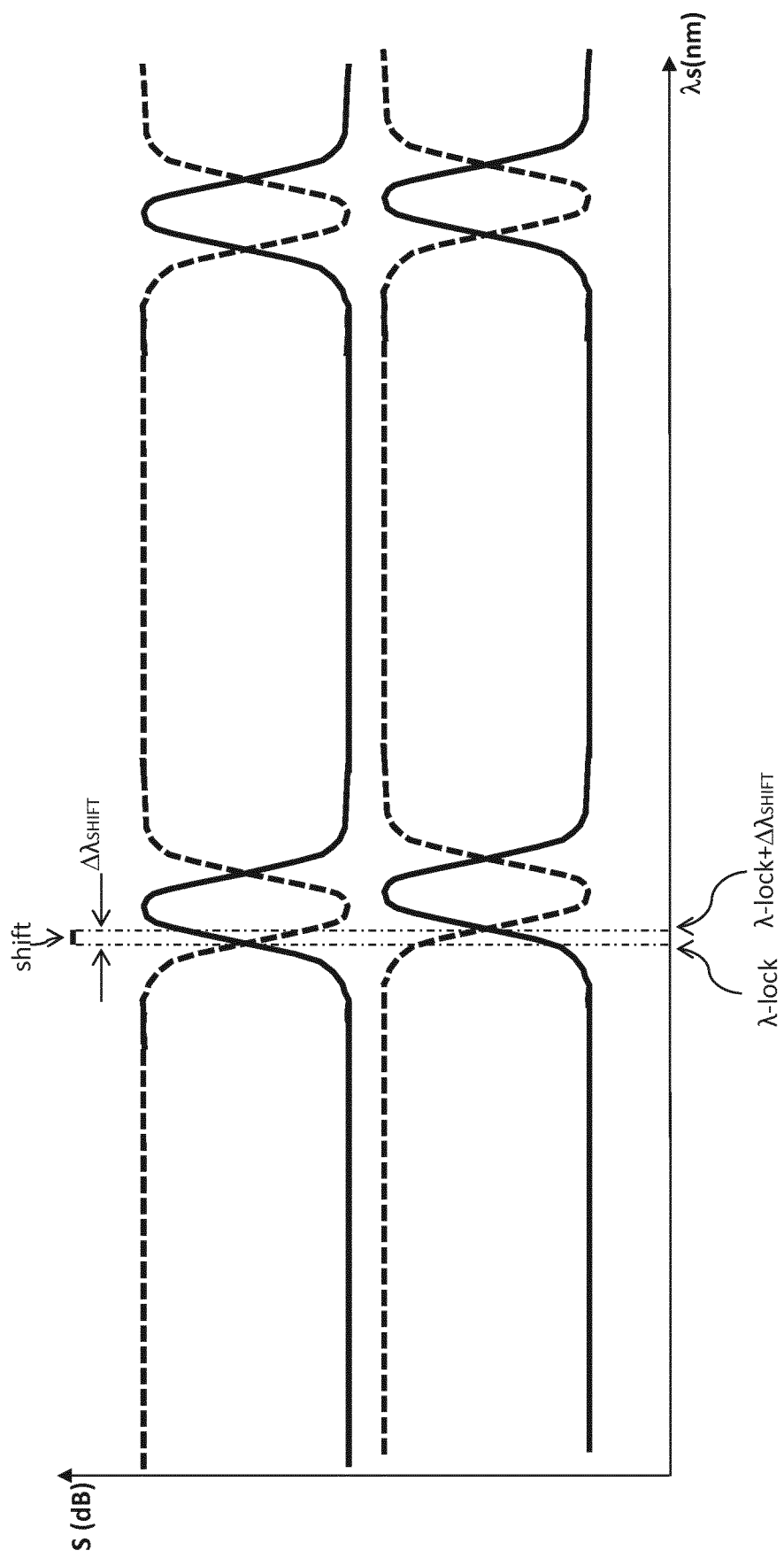
FIG. 3 is a graphical diagram schematically illustrating a control operation of the optoelectronic device according to FIG. 1.

FIGS. 2 and 3 schematically illustrate operation of the control loop 901 of the control unit 9.

FIG. 2 schematically shows the trend of the optical power curves $S_A$, $S_B$ for the light radiations $L_{T1}$, $L_{T2}$ received by the detectors 4, 6 (when the control loop 901 is active) and the optical power curve Ss of the light radiation emitted by the light source 2.

The optical power curves $S_A$, $S_B$ can advantageously be calculated according to the following relations that express a physical-mathematical model of known type (lorentzian profile) for the optical resonator 5 (FIG. 2):

$$S_A(\lambda) = P_A - (P_A - P_B)/(1 + (2(\lambda - \lambda r)/\Delta\lambda r)^2)$$

$$S_B(\lambda) = P_B + (P_A - P_B)/(1 + (2(\lambda - \lambda r)/\Delta\lambda r)^2)$$

where $P_A$, $P_B$ are respectively the maximum optical power of the light radiation $L_{T1}$ and the minimum optical power of the light radiation $L_{T2}$.

As it is possible to observe from FIG. 2, the optical power curves $S_A$, $S_B$ are substantially complementary with respect to the optical power curve $S_S$.

Given that the control loop 901 is active, the trend of both the optical power curves $S_A$, $S_B$ is influenced by the action of the optical resonator 5.

The optical power curves $S_A$, $S_B$ in fact show periodic resonance peaks, at multiple wavelengths of the resonance wavelength $\lambda r$ of the optical resonator 5.

Each resonance peak has a width $\Delta\lambda r$ and a merit factor $Q = (\lambda r/\Delta\lambda r)$.

The distance $d_r$ between two successive resonance peaks can be given by the relation:

$$d_r = \lambda r^2/(2\pi r^* \text{neff})$$

where r is the radius of the ring optical path 51, neff is the refraction index of the material at the active surface 52 and $\lambda r$ is the resonance wavelength of the optical resonator 5.

As can be observed, according to the invention, in response to the first control signals C1 provided by the control unit 9, the light source 2 emits a light radiation $L_E$ having a wavelength $\lambda s$ such that the difference of optical power $\Delta S$ between the light radiations $L_{T1}$, $L_{T2}$ takes a minimum value ($\Delta S = 0$).

It is evident how this condition is produced at a crossing point P-lock between the optical power curves $S_A$, $S_B$ around the resonance wavelength $\lambda r$ of the optical resonator 5 (FIG. 2).

The wavelength $\lambda$-lock corresponding to this crossing point is given by the following relation:

$$\lambda\text{-lock} = \lambda r^*(1 - \Delta\lambda r/2\lambda r) = r^*(1 - 1/2Q)$$

where $\lambda r$ is the resonance wavelength of the optical resonator 5, $\Delta\lambda r$ is the width of the related resonance peak and $Q = \lambda r/\Delta\lambda r$ is the merit factor of the related resonance peak.

The above clearly shows how the control unit 9 is adapted to control the light source 2 so that the wavelength $\lambda_S$ of the light radiation emitted by this latter continuously follows a wavelength (around the resonance wavelength $\lambda r$ of the optical resonator 5) at which the difference of optical power $\Delta S$ between the light radiations $L_{T1}$, $L_{T2}$ takes a minimum value ($\Delta S = 0$).

The control unit thus provides a fully differential control of the wavelength $\lambda s$ of the light radiation emitted by light source 2. This is an important advantage of the invention as it allows achieving an improved common mode noise rejection with respect to known solutions of the state of the art.

It must be noted that the crossing point P-lock between the optical power curves $S_A$, $S_B$ is around the point of maximum slope of the optical power curves $S_A$, $S_B$. This allows maximization of the feedback gain and a further optimization of the common mode noise rejection. Moreover, unlike known solutions, for example the solution proposed by the patent U.S. Pat. No. 9,080,953, the response time takes minimum values at the wavelength $\lambda$-lock.

As indicated above, absorption of the target substance by the active surface 52 of the optical resonator 5 determines a variation (shift) $\Delta\lambda_{SHIFT}$ of the resonance wavelength $\lambda r$ of the optical resonator and, consequently, a corresponding variation of the wavelength of the light radiation $L_{T2}$ that travels along the optical path 51.

The extent of this variation $\Delta\lambda_{SHIFT}$ depends on the quantity of target substance absorbed by the material of the active surface 52, as illustrated above.

In response to absorption of the target substance by the active surface 52 of the optical resonator 5, as illustrated in FIG. 3, the light source 2 thus emits a light radiation having a new wavelength $\lambda$-lock+$\Delta\Delta\lambda_{SHIFT}$, at which the difference of optical power $\Delta S$ between the light radiations $L_{T1}$, $L_{T2}$ takes a minimum value ($\Delta S = 0$).

In practice, in response to an absorption of the target substance, there is a shift $\Delta\lambda_{SHIFT}$ of the wavelength of the crossing point P-lock between the optical power curves $S_A$, $S_B$ around the resonance wavelength $\lambda r$ of the optical resonator 5 (FIG. 3).

According to a preferred embodiment, illustrated in the aforesaid figures, the first wave-guide 11 comprises a movable end 111 in proximal position with respect to the first active surface 31 of the optical coupler 3.

Preferably, the movable end 111 of the wave-guide 11 is able to move at least along a motion plane it parallel to the first active surface 31 and at a predefined distance Z0 (for example Z0 = 15 μm) from the active surface 31, according to an axis Z perpendicular to this latter.

Preferably, the optoelectronic device 1 comprises an actuation device 8 operatively coupled to the movable end 111 of the wave-guide 11 to move this movable end along the motion plane π. For example, the actuation device 8 can be a micro-motor of stepping type capable of moving the movable end 111 of the wave-guide 11 with movements in the order of the 100 nm.

Preferably, the optoelectronic device 1 comprises a second control loop 902 comprising the photonic circuit 10 and a second control module 94 of the control unit 9 operatively connected to the detector 4 to receive the detection signals S1 provided by these latter.

The control module 94 is adapted to receive the detection signals S1 and to provide, in response to the aforesaid detection signals, second control signals C2 for the actuation device 8 to move the movable end 111 of the wave-guide 11 and adjust the position of this latter at least along the motion plane π.

The solution illustrated above is very advantageous given that it allows optimization of the transfer of optical power from the light source 2 to the optical coupler 3, in particular when this latter consists of an optical grating coupler (FIG. 5).

By moving the movable end 111 of the wave-guide 11 along a motion plane π, it is possible to align with high precision the light cone exiting from the wave-guide 11 with the active surface 31 of the optical coupler 3. This allows a considerable increase in the measurement resolution of the optoelectronic device.

Moreover, the inventors have verified how the distance Z0 of the motion plane π from the active surface 31 is not critical in order to optimize the transfer of optical power from the light source 2 to the optical coupler 3.

The movement of the movable end 111 can thus take place on a plane rather than three dimensions, with considerable advantages in terms of simple construction and positioning precision.

Preferably, the control unit 9 is adapted to execute a calibration procedure of the position of the movable end 111 of the wave-guide 11 (FIG. 5).

Preferably, the calibration procedure is executed by the second control loop 902.

Preferably, the calibration procedure is executed with the movable end in an initial position P0=X0,Y0 (the coordinate Z0 is preferably maintained fixed for the above reasons).

Preferably, the calibration procedure is executed with the first control loop 901 deactivated and with the light source 2 that initially emits a light radiation $L_E$ having a calibration wavelength λstart at which the optical power S1 of the first light radiation $L_{T1}$ received by the first detector 4 takes a maximum absolute value (FIG. 2).

The wavelength λstart can be obtained acting directly on the light source 2 (for example by means of the control module 93) or on a thermoregulation circuit operatively coupled to the photonic circuit 10.

Preferably, in a first calibration step of the calibration procedure, the control module 94 controls (by means of suitable control signals C2) the actuation device 8 to move the movable end 111 along a first motion axis Y=Y0 of the motion plane it until reaching a first calibration position P1=(X1,Y0) at which the optical power $S_A$ of the first light radiation $L_{T1}$ received by the detector 4 takes a maximum value.

Preferably, in a second calibration step of the calibration procedure, the control module 94 controls (by means of suitable control signals C2) the actuation device of 8 to move the movable end 111 along a second motion axis X=X1 of the motion plane π, perpendicular to the aforesaid first motion axis Y0, until reaching a second calibration position P2=(X1,Y1) at which the optical power $S_A$ of the first light radiation $L_{T1}$ received by the detector 4 takes a maximum value.

Preferably, in the subsequent steps of the calibration procedure described above, the movement of the movable end 111 is implemented with stepping movements (positive or negative in the order of 100 nm) repeated cyclically until reaching the optimal calibration position along the respective motion axis.

According to a further aspect of the invention, illustrated in the aforesaid figures, the optoelectronic device 1 is provided with a control arrangement to control the temperature of the integrated circuit 100.

Preferably, the optoelectronic device 1 comprises a temperature sensor circuit 71 (preferably integrated with the photonic circuit 10) adapted to provide third detection signals T (of electrical type) indicative of the temperature of the integrated circuit 100.

Preferably, the optoelectronic device 1 comprises a control module 95 (preferably comprised in the control unit 9) and a heating circuit 70 operatively coupled to the integrated circuit 100 to heat this latter, when required.

Preferably, the heating circuit 70 comprises one or more Peltier cells operatively coupled to a voltage source (for example the control unit 9) capable of providing a suitable regulation voltage for the aforesaid cells.

The control module 95, the temperature sensor circuit 71 and heater 70 form a third control loop 903 for regulating the temperature of the integrated circuit 100.

Preferably, the control module 95 is operatively connected to the temperature sensor 71 to receive the detection signals T provided by these latter.

The control module 94 is adapted to receive the detection signals T and to provide, in response to the aforesaid detection signals, third control signals C3 for the heating circuit 70.

Figure 4:
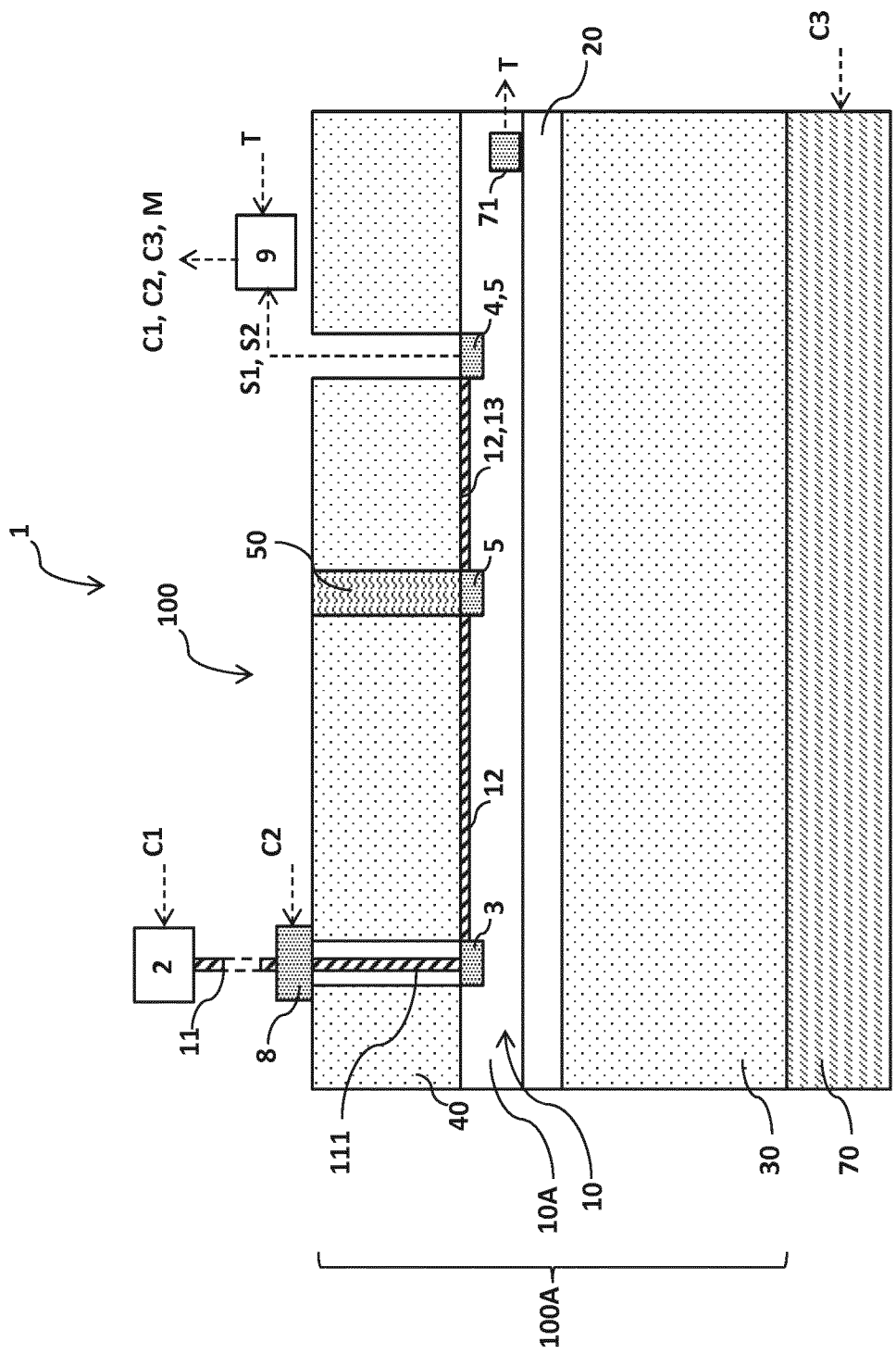
FIG. 4 represents an embodiment of the integrated electronic circuit according to FIG. 1, comprising a multilayer structure made of semiconductor material, for example Si.

According to a preferred embodiment, illustrated in the aforesaid figures, the integrated electronic circuit 100 comprises a multilayer structure 100A made of semiconductor material, for example Si (FIG. 4).

The multilayer structure 100A can be produced by means of known techniques for processing semiconductor materials, for example SOI (Silicon On Insulator) wafers.

Preferably, the multilayer structure 100A comprises a substrate 30 made of semiconductor material (for example Si-bulk having a thickness generally variable from 600 um to 200 um)

Preferably, the multilayer structure 100A comprises a layer of insulating material 20 (for example $SiO_2$) superimposed on the substrate 30. For example, the layer of insulating material can be formed by a Buried Oxide Layer of a wafer of SOI type with a thickness comprised between 750 nm and 2 μm.

Preferably, the multilayer structure 100A comprises a layer of semiconductor material 10A (for example Si-epi with a thickness between 300 nm and 2 μm) superimposed on the layer of insulating material 20.

The integrated photonic circuit 10 is advantageously produced at the layer 10A.

The layer 10A of the multilayer structure 100A thus advantageously comprises, in the form of integrated circuits, at least the optical coupler 3, the optical resonator 5, the waveguides 12, 13 and the detectors 4, 6.

Preferably, the temperature sensor circuit 71 is also integrated with the photonic circuit 10 and is produced at the layer 10A of the multilayer structure 100A.

Preferably, the integrated electronic circuit 100 comprises a protective layer 40 made of plastic material superimposed on the layer 10A of the multilayer structure 100A.

The protective layer 40 is advantageously provided with suitable openings to allow the fluid 50 to come into contact with the active surface of the optical resonator 5, to allow optical coupling between the light source 2 and the optical coupler 3 of the photonic circuit 10 and to allow electrical connection between the detectors 4, 6 and the control unit 9.

The optoelectronic device according to the invention has considerable advantages with respect to state of the art devices.

The optoelectronic device 1 uses a closed control loop 901 that allows the light source 2 to emit light radiation with wavelength coupled to the resonance wavelength $λ_r$ of the optical resonator 5.

As illustrated in FIGS. 2-3, the light source 2 is forced to emit light radiation at wavelengths λs=λ-lock for coupling with the resonance wavelength $λ_r$ of the optical resonator 2, at which the optical power curves $S_A$, $S_B$ take a maximum slope (crossing point P-lock).

This allows a relatively high loop gain to be obtained and therefore considerable improvement of the measurement accuracy and the stability of the feedback control.

The optoelectronic device 1 uses a single optical resonator 5 to generate an error signal of differential type used by the control loop 901 to control the light source 2. This allows a high rejection of any common mode noise (for example due to variations of temperature, vibrations, etc.) to be obtained, with consequent increase of the accuracy and of the measurement resolution.

The optoelectronic device 1 is advantageously provided with a motion system of the wave-guide 11 that couples the light source 2 with the photonic circuit 10. It is thus possible to considerably reduce the coupling losses due to any misalignments between the light cone emitted by the wave-guide 11 and the active surface 31 of the optical coupler 3.

The optoelectronic device 1, in particular the photonic circuit 10, and more generally the integrated circuit 100, is particularly suitable for mass production (batch processing) by means of known techniques for processing semiconductor materials. Moreover, the integrated circuit 100, in particular the photonic circuit 10, is easy to operatively couple with the control unit 9. The optoelectronic device 1 therefore has a very compact structure, easy to produce industrially at relatively limited costs.

The optoelectronic device 1 is particularly suitable for use in an apparatus for the detection of substances dispersed in a fluid or in an apparatus of bio-medical type.

An apparatus of this type may comprise, for example, a sample preparation unit to collect a process fluid to analyse, a micro-fluidic chamber and a peristaltic pump to force the collected process fluid to flow from the sample preparation unit into the micro-fluidic chamber.

In the microfluidic chamber, the process fluid is brought into contact with the active surface of the optoelectronic device 1.

The process fluid is conveniently pumped into the microfluidic chamber with suitable speed and flow in order to maximize the binding probability of possible low-concentration target molecules with the active surface 52 of the optoelectronic device 1.

The first measurement signals M (which may be indicative of a concentration value or a binding event count) provided by the optoelectronic device 1 may be conveniently processed to obtain an analyte concentration metric by a suitable data-analysis software.

As it adopts a fully differential control system, the optoelectronic device 1 ensures high performance in terms of accuracy and measurement resolution. For example, it is capable of detecting dispersed substances with very low concentration values, for example tens of particles (of dimensions below 100 nm) per millilitre (ml). For many types of target substances, the optoelectronic device 1 is able to offer a numerical count of the molecules in a fluid.

The invention claimed is:

1. An optoelectronic device for detection of a target substance dispersed in a fluid, the device comprising:
   a light source adapted to emit a light radiation having a tunable wavelength ($\lambda$s);
   an integrated electronic circuit comprising a photonic circuit operatively coupled with said light source;
   a control unit operatively coupled with said light source and said photonic circuit;
   wherein said photonic circuit comprises:
   an optical coupler comprising a first active surface optically coupled with said light source to receive a light radiation emitted by said light source;
   a first detector optically coupled with said optical coupler to receive a first light radiation corresponding to a first portion of a light radiation transmitted by said optical coupler, said first detector being adapted to provide first detection signals indicative of an optical power of said first light radiation, said first detector being operatively coupled with said control unit to transmit said first detection signals to said control unit;
   an optical resonator optically coupled with said optical coupler to convey and transmit a second light radiation corresponding to a second portion of the light radiation transmitted by said optical coupler, said optical resonator comprising a ring optical path and, in at least a portion of said optical path, a second active surface adapted to come into contact with said fluid and comprising a material capable of selectively absorbing said target substance, a resonance wavelength ($\lambda_r$) of said optical resonator varying as a function of the quantity of said target substance absorbed by said second active surface;
   a second detector optically coupled with said optical resonator to receive the second light radiation transmitted by said optical resonator, said second detector being adapted to provide second detection signals indicative of the optical power of said second light radiation, said second detector being operatively coupled with said control unit to transmit said second detection signals to said control unit;
   said control unit configured to receive and process said first and second detection signals and provide, in response to said first and second detection signals, first control signals to tune the wavelength ($\lambda$s) of the light radiation emitted by said light source wherein an optical power difference ($\Delta$S) between said first and second light radiation is set to zero.

2. The optoelectronic device of claim 1, wherein said control unit is configured to provide, in response to said first and second detection signals, first measurement signals indicative of a presence or concentration of said target substance in said fluid.

3. The optoelectronic device of claim 1, further comprising a first wave-guide adapted to optically couple said optical coupler with said light source.

4. The optoelectronic device of claim 3, further comprising a second wave-guide adapted to optically couple said optical coupler with said first detector and said optical resonator.

5. The optoelectronic device of claim 4, further comprising a third wave-guide adapted to optically couple said optical resonator with said second detector.

6. The optoelectronic device of claim 3, wherein said first wave-guide comprises, in proximal position with respect to the first active surface of said optical coupler, a movable end capable of moving at least along a motion plane parallel to said first active surface.

7. The optoelectronic device of claim 6, further comprising an actuation device operatively coupled with said movable end to move said movable end along said motion plane.

8. The optoelectronic device of claim 7, wherein the control unit is further configured to receive said first detection signals and provide, in response to said first detection signals, second control signals for said actuation device to tune the position of said movable end.

9. The optoelectronic device of claim 8, wherein said control unit is further configured to calibrate the position of said movable end, by:
commanding said actuation device to move said movable end along a first motion axis of said motion plane to reach a first calibration position at which the optical power of the first light radiation received from said first detector takes a maximum value; and
commanding said actuation device to move said movable end along a second motion axis of said motion plane, perpendicular to said first motion axis, to reach a second calibration position at which the optical power of the first light radiation received from said first detector takes a maximum value.

10. The optoelectronic device of claim 1, further comprising a wave-guide adapted to optically couple said optical coupler with said first detector and said optical resonator.

11. The optoelectronic device of claim 1, further comprising a wave-guide adapted to optically couple said optical resonator with said second detector.

12. The optoelectronic device of claim 1, wherein said control unit is configured to provide said first control signals by:
in response to receiving said first and second detection signals, providing second measurement signals indicative of an optical power difference ($\Delta S$) between said first and second light radiation;
receiving said second measurement signals and providing, in response to said second measurement signals, regulation signals indicative of a reference wavelength for the light radiation emitted by said light source, wherein the optical power difference ($\Delta S$) between said first and second light radiation is set to zero at said reference wavelength; and
receiving said regulation signals and providing, in response to said regulation signals, said first control signals.

13. The optoelectronic device of claim 1, wherein said integrated electronic circuit comprises a temperature sensing circuit adapted to provide third detection signals indicative of a temperature of said integrated electronic circuit, and
said control unit is further configured to receive said third detection signals and provide, in response to said third detection signals, third control signals for a heating circuit of said optoelectronic device, said heating circuit being operatively coupled with said integrated electronic circuit to heat said integrated electronic circuit.

14. The optoelectronic device of claim 1, wherein said light source is a laser light source.

15. An apparatus for detecting a target substance dispersed in a fluid, said apparatus comprising the optoelectronic device of claim 1.

16. A bio-medical apparatus comprising the optoelectronic device of claim 1.

17. The bio-medical apparatus of claim 16, further comprising:
a sample preparation unit adapted to collect a process fluid to analyze;
a micro-fluidic chamber; and
a peristaltic pump adapted to force the collected process fluid to flow from the sample preparation unit into the micro-fluidic chamber.

18. The bio-medical apparatus of claim 17, wherein the process fluid in the micro-fluidic chamber is brought into contact with the second active surface of the optoelectronic device.

19. The bio-medical apparatus of claim 18, wherein a speed and flow of the process fluid being pumped into the micro-fluidic chamber is determined in order to maximize a binding probability of low-concentration target molecules with the second active surface of the optoelectronic device.

* * * * *